United States Patent [19]

Huss, Jr. et al.

[11] Patent Number: 4,888,105
[45] Date of Patent: Dec. 19, 1989

[54] PROCESS FOR THE DEHYDROCYCLIZATION OF ACYCLIC HYDROCARBONS AND CATALYST COMPOSITION THEREFOR

[75] Inventors: Albin Huss, Jr., Chadds Ford, Pa.; Sowmithri Krishnamurthy, Cherry Hill; William D. McHale, Swedesboro, both of N.J.

[73] Assignee: Mobil Oil Corporation, New York, N.Y.

[21] Appl. No.: 156,067

[22] Filed: Feb. 16, 1988

[51] Int. Cl.$^4$ .................. C10G 35/085; C10G 35/095
[52] U.S. Cl. ................................. 208/137; 208/138; 585/407; 585/418; 585/419; 585/434
[58] Field of Search ............... 208/137, 138; 585/419, 585/434, 407, 410, 418

[56] References Cited

U.S. PATENT DOCUMENTS

| | | | |
|---|---|---|---|
| 3,216,789 | 11/1965 | Breck et al. | 423/328 |
| 3,867,512 | 2/1975 | Young | 423/118 |
| 4,104,320 | 8/1978 | Bernard et al. | 208/138 |
| 4,435,283 | 3/1984 | Buss et al. | 208/138 |
| 4,456,527 | 6/1984 | Buss et al. | 208/89 |
| 4,517,306 | 5/1985 | Buss | 502/66 |
| 4,530,824 | 7/1985 | Arika et al. | 423/329 |
| 4,544,539 | 10/1985 | Wortel | 423/328 |
| 4,547,472 | 10/1985 | Van Nordstrand | 502/74 |
| 4,554,146 | 11/1985 | Vaughan | 423/118 |
| 4,650,565 | 3/1987 | Jacobson et al. | 208/138 |
| 4,746,764 | 5/1988 | Lambert et al. | 208/138 |
| 4,822,941 | 4/1989 | Baillargeon et al. | 208/135 |

FOREIGN PATENT DOCUMENTS

| | | | |
|---|---|---|---|
| 0202797 | 5/1985 | European Pat. Off. | 502/77 |
| 2116450 | 9/1983 | United Kingdom | 502/66 |

*Primary Examiner*—Anthony McFarlane
*Attorney, Agent, or Firm*—Alexander J. McKillop; Charles J. Speciale; Dennis P. Santini

[57] ABSTRACT

The dehydrocyclization of a feed containing one or more acyclic hydrocarbons capable of undergoing ring closure to provide aromatic hydrocarbons is accomplished by contacting the feed under dehydrocyclization conditions with a zeolite L dehydrocyclization catalyst which is substantially free of zeolite T and which contains at least one Group VIII metal component, thereby converting at least a portion of the acyclic hydrocarbon content of the feed to aromatic compound(s). Use of the foregoing zeolite L dehydrocyclization catalyst has been found to result in less non-selective hydrocracking of naphtha range materials to gaseous hydrocarbons and greater conversion of low octane paraffins to high octane aromatics than that achieved with a zeolite L synthesized by a prior procedure which results in the co-production of zeolite T contaminant.

10 Claims, No Drawings

PROCESS FOR THE DEHYDROCYCLIZATION OF ACYCLIC HYDROCARBONS AND CATALYST COMPOSITION THEREFOR

BACKGROUND OF THE INVENTION

This invention relates to the dehydrocyclization of acyclic hydrocarbons to provide aromatics employing as catalyst therefor a Group VIII metal-containing zeolite L which has been synthesized in a unique manner.

Catalytic reforming is a well known type of petroleum refinery operation which is employed to improve the octane rating of straight run gasolines. It involves converting naphtha fractions, i.e., paraffins which possess low octane ratings, to aromatics which possess high octane values. Hydrocarbon conversion reactions occurring during reforming include dehydrogenation of cyclohexanes to aromatics, dehydroisomerization of alkylcyclopentanes to aromatics, dehydrocyclization of acyclic hydrocarbons to aromatics, dealkylation of alkylbenzenes, isomerization of paraffins and hydrocracking reactions which product light gaseous hydrocarbons such as methane, ethane, propane and butanes.

Dehydrocyclization of acyclic hydrocarbons to provide aromatics is one of the principal reactions involved in reforming. Catalysts based on zeolite L are known to be more selective than other large pore zeolites for the dehydrocyclization reaction.

According to U.S. Pat. No. 4,435,283, paraffins undergo dehydrocyclization in the presence of hydrogen at a temperature of 430°–550° C. and in the presence of zeolite L which possesses cations of which at least 90% are alkali metal ions and at least one Group VIII metal. In the dehydrocyclization process described in U.S. Pat. No. 4,456,527, a hydrotreated, desulfurized hydrocarbon feed is contacted with zeolite L in the presence of a diluent, preferably hydrogen, at elevated pressure (1 atm to 500 psig) and temperature (450°–550° C.) and a liquid hourly space velocity (LHSV) of from about 0.1 to about 10 hr.$^{-1}$ Additional disclosures of the use of zeolite L in catalytic reforming/dehydrocyclization can be found in U.S. Pat. Nos. 4,517,306, 4,547,472 and 4,544,439 and UK patent application No. 2,116,450.

With the exception of U.S. Pat. No. 4,544,539 the foregoing prior art contemplates the use of zeolite L which has been prepared by the procedure described in U.S. Pat. No. 3,216,789.

Commonly assigned copending U.S. patent application Ser. No. 124,657 filed Nov. 24, 1987 describes a process for producing zeolite L free of zeolite T contaminant, the latter being a by-product when utilizing the zeolite L synthesis procedure of U.S. Pat. No. 3,216,789. Although the zeolite L produced by the process of U.S. patent application Ser. No. 124,657 is disclosed to be useful in dehydrogenating hydrocarbon compounds and converting paraffins to aromatics, no mention is made of employing the zeolite in association with a metal component much less a Group VIII metal component.

It is an object of this invention to provide a hydrocarbon conversion process and catalyst composition therefor which is selective for the dehydrocyclization of low octane paraffins to high octane aromatics.

It is a particular object of the invention to utilize a Group VIII metal-containing zeolite L catalyst composition for such dehydrocyclization, the zeolite L having been synthesized in the manner disclosed in aforesaid U.S. patent application Ser. No. 124,657.

SUMMARY OF THE INVENTION

By way of achieving the foregoing and other objects of the invention, a process is provided for the dehydrocyclization of a feed containing one or more acyclic hydrocarbons capable of undergoing ring closure to provide aromatic hydrocarbons which comprises contacting the feed under dehydrocyclization conditions with a zeolite L dehydrocyclization catalyst which is substantially free of zeolite T and which contains at least one Group VIII metal component, thereby converting at least a portion of the acyclic hydrocarbon content of the feed to aromatic compound(s).

The use of Zeolite L synthesized in the manner described in U.S. patent application Ser. No. 124,657 in the foregoing dehydrocyclization process has been found to result in less non-selective hydrocracking of naphtha range materials to gaseous hydrocarbons and greater conversion of low octane paraffins to high octane aromatics.

DESCRIPTION OF THE PREFERRED EMBODIMENTS

The catalyst employed in the dehydrocyclization process of this invention is a zeolite L which has been synthesized in accordance with the procedure described in U.S. patent application Ser. No. 124,657 and thereafter incorporated with one or more Group VIII metals.

As described in U.S. patent application Ser. No. 124,657, the zeolite L synthesis can be undertaken at high solids loading, particularly of the amorphous silicon source, in the zeolite synthesis reaction mixture. "Loading" in the synthesis reaction mixture is defined by the fraction $$\frac{\text{Weight of Silica and Alumina}}{\text{Weight of Total Reaction Mixture}}$$

and "% loading" is defined by multiplying that fraction by 100%, i.e., $$100\% \frac{\text{Weight of Silica and Alumina}}{\text{Weight of Total Reaction Mixture}}$$

Generally, the percent loading will be greater than 15%. Practically, the % loading can exceed about 20% and preferably will be at least about 30%. These high loadings maximize the zeolite yield per reaction mixture.

This high loading can be achieved by providing a source of silicon which has been formed by continuously precipitating that source of silicon for the zeolite synthesis. That continuous precipitation allows for the provision of a silicon-containing precipitate, the particle size of the precipitate ranging from 1 to about 500 microns, which exceeds that particle size at which silica gel formation is possible.

The precipitate, the source of silicon in the zeolite L synthesis, is formed from a solution of a soluble silicon source. Conveniently, the solution is an aqueous solution at a pH ranging from 9 to 12. The source of soluble silicon can be any soluble silicate and is preferably sodium silicate. The precursor is formed by continuous precipitation from the solution phase. Accordingly, precipitation comprises initiating precipitation and maintaining said precipitation. More particularly, the precipitation step is continuous. Alteration of the composition of the solution of soluble silicon source is undertaken by introducing a precipitating reagent. In one embodiment, the precipitating reagent is a source of acid. Thus, the precipitating reagent can be an acid solution. The acid of the solution may be any mineral acid, such as $H_2SO_4$, HCl, $HNO_3$, etc. The acid solution can have a pH ranging from essentially 0 to about 6. Thus, in one embodiment precipitation can be effected by acid neutralization of a basic solution of a silicate.

In one of the two alternative embodiments, the soluble silicon source, e.g., silicate, can be precipitated alone in the absence of sources of other zeolitic framework elements. In this embodiment, both the precipitating reagent and the solution of silicate can be free of intentionally added alumina or alumina source. That is, no aluminum is deliberately added to the precipitation reaction mixture, in this embodiment; however, aluminum is ubiquitous and the presence of such a material in minor amounts is due to impurities in the precursors of the reactants or impurities extracted from the reaction vessel; thus, when no source of alumina is added in the alternative embodiment, the amount of alumina in the precipitate generally will be less than about 0.5 and generally lower than 0.2 weight percent. The foregoing embodiment is preferred at this time for the reason that it allows greater flexibility in varying the ratios of zeolite elemental components in the zeolite product realized during the crystallization stage in which the silicate is subjected to zeolite production. However, precipitation can be coprecipitation in the presence of soluble sources of other zeolite framework elements including aluminum, gallium, indium, boron, iron and chromium. The soluble source of these other zeolitic framework components can be, e.g., nitrates. The coprecipitation product would be an amorphous, e.g., aluminosilicate, gallosilicate, borosilicate, ferrosilicate. Alternatively, soluble sources of aluminum, gallium, indium, boron, iron and/or chromium can be added with the precipitated silica precursor to the zeolite crystallization stage.

Continuous precipitation of the amorphous silicon zeolite precursor comprises continuously introducing the solution of soluble silicon source and continuously introducing the precipitating reagent to a reaction zone while maintaining a molar ratio of silica source to precipitating reagent substantially constant. In one embodiment, the precipitating reagent and the silicate source are introduced simultaneously into the reaction zone.

The precipitate precursor comprises agglomerated solids in the shape of microspheres. Suspensions of these particles exhibit low viscosities at high solids loadings in subsequent processing, including zeolite synthesis, for example, even at solids loading equal to or greater than 20–30% and even at 35% solids. This is in marked contrast to non-controlled neutralization which results in a solid, non-stirrable mass. The particle size of the silica precipitate ranges between about 1–500 microns but the average size is about 50–100 microns.

Other conditions affecting precipitation include time, pH and temperature. The temperature of the precipitation mixture can range from about 80° to about 300° F. (about 27° C. to about 150° C.). The time of contact of the solution of silicon source and the precipitating reagent can range from about 10 minutes to several hours at pH maintained from about about 6 to about 11. Generally, the precipitate is processed by isolating it, e.g., by filtration, and removing soluble contaminants therefrom, by washing and/or ion exchange. This stage can be considered a solids consolidation step.

Use of that source of silicon in the zeolite L crystallization of the invention can be either in a batch or continuous process. The zeolite L synthesis reaction mixture has a composition in terms of molar ratio of oxides as follows

| | |
|---|---|
| $SiO_2/Al_2O_3$ | 6 to 30 |
| $OH^-/SiO_2$ | 0.3 to 0.8 |
| $K^+/(K^+ + Na^+)$ | 0.3 to 1 |
| $H_2O/OH^-$ | 10 to 50 |
| seeds | 0 to 10% | wherein seeds are crystals of zeolite L. The crystal size of zeolite L produced in that non-organic system is small, the dimensions of the crystal being less than 1 micron, generally less than 0.5 micron.

If the zeolite L is to contain alumina (or gallium, indium, boron, iron and/or chromium) in appreciable amounts, the aluminum source is preferably added to the zeolite L reaction mixture, rather than to the solution from which the source of silicon, the silicate precipitate, is formed.

To make zeolite L free of zeolite T (offretite type), the synthesis reaction mixture will have a composition in terms of mole ratio of oxides, as follows:

| | |
|---|---|
| $SiO_2/Al_2O_3$ | 6 to 30 |
| $OH^-/SiO_2$ | 0.3 to 0.8 |
| $RN/Al_2O_3$ | 0.2 to 2 |
| $K^+/(K^+ + Na^+)$ | 0.3 to 1 |
| $H_2O/OH^-$ | 10 to 50 |
| seeds | 0 to 10% | wherein R is a source of tetraalkylammonium cation, preferably tetraethylammonium, tetrapropylammonium, tetrabutylammonium cation. The halide form of the cation may be employed, preferably bromide. In this system, not only is zeolite L produced free of zeolite T (offretite type) contaminant, but is also in the form of small crystals, the average dimension of the crystals being less than about 1 micron and generally less than 0.5 microns. That is, in terms of a crystal defined by 3 dimensions, the largest of the three dimensions is on the average less than about 1 micron and generally less than about 0.5 microns.

The synthesis of zeolite L can be undertaken at temperatures ranging from about 200° to about 320° F. Crystallization can be undertaken at static, but preferably stirred, conditions in, for example, stainless steel autoclaves. At temperatures of about 200° to about 320° F., crystallization can take from about 2-3 hours to about 150 days. Zeolite L crystals can be separated from the reaction mixture by filtration or other suitable technique. In all cases, synthesis of the desired crystals may be facilitated by the presence of at least about 0.001 percent, preferably at least about 0.10 percent and still more preferably at least about 1.0 percent, seed crystals (based on total solids) of a previously prepared crystalline product. The source of seeds may be a slurry from a previous crystallization, processed or unprocessed, recycled to the crystallizer vessel.

Ion exchange of zeolite L can be conducted to effect ammonium exchange at acidic sites. The source of the ammonium ion is not critical; thus the source can be ammonium hydroxide or an ammonium salt such as ammonium nitrate, ammonium sulfate, ammonium chloride and mixtures thereof. These reagents are usually in aqueous solutions; by way of illustration, aqueous solutions of 1N $NH_4OH$, 1N $NH_3NO_3$, 1N $NH_4Cl$ and 1N $NH_4Cl/NH_4OH$ have been used to effect ammonium ion exchange on these and similar materials. The pH of the ion exchange is not critical but is generally maintained at from about 7 to about 12. Ammonium exchange may be conducted for period of time ranging from about 0.5 to about 20 hours at a temperature ranging from ambient up to about 100° C. The ion exchange may be conducted in multiple stages. Calcination of the ammonium exchanged product will produce the zeolite in its acid form. Calcination can be effected at temperatures up to about 600° C.

The zeolite L synthesized in the foregoing manner is provided with one or more Group VIII metals, e.g., nickel, ruthenium, rhodium, palladium, iridium or platinum. Preferred Group VIII metals are iridium, and particularly platinum, which are more selective with regard to dehydrocyclization and are also more stable under the dehydrocyclization treatment conditions than other Group VIII metals. The preferred percentage of platinum in the catalyst is between about 0.1 wt. % and about 5 wt. %.

The Group VIII metals are introduced into the zeolite L by synthesis, impregnation or exchange in an aqueous solution of appropriate salt. When it is desired to introduce two or more Group VIII metals into the zeolite, the operation may be carried out simultaneously or sequentially for each metal. By way of example, platinum can be introduced by impregnating the zeolite with an aqueous solution of tetraamineplatinum (II) nitrate, chloroplatinic acid, chloroplatinous acid, dinitrodiamino-platinum or tetraamineplatinum (II) chloride. In an ion exchange process, platinum can be introduced by using cationic platinum complexes such as tetraamineplatinum (II) nitrate.

It may be advantageous to associate the zeolite L dehydrocyclization catalyst herein with at least one alkaline earth metal component, specifically, barium, strontium or calcium with barium being preferred. The alkaline earth metal can be present at a level of from about 0.1 wt. % to about 35 wt. % and can be incorporated into the zeolite by synthesis, impregnation or ion exchange, e.g., in accordance with the procedure described in U.S. Pat. No. 4,547,472, the contents of which are incorporated by reference herein.

It is often desirable to bind the zeolite L with a matrix material which is resistant to the temperatures and other conditions employed in the dehydrocyclization process herein. Such matrix materials include catalytically active and inactive materials and synthetic or naturally occurring zeolites as well as inorganic materials such as clays, silica and/or metal oxides, e.g., alumina. The latter may be either naturally occurring or in the form of gelatinous precipitates, sols or gels including mixtures of silica and metal oxides. Use of a material in conjunction with zeolite L, i.e., combined therewith, which is active, may enhance the conversion and/or selectivity of the catalyst in certain organic conversion processes. Inactive materials suitably serve as diluents to control the amount of conversion in a given process so that products can be obtained economically and orderly without employing other means for controlling the rate or reaction. Frequently, crystalline silicate materials have been incorporated into naturally occurring clays, e.g., bentonite and kaolin. These materials, i.e., clays, oxides, etc., function in part as binders for the catalyst. It is desirable to provide a catalyst having good physical strength since in petroleum refinery processing the catalyst is often subjected to conditions which tend to break the catalyst down into powder-like materials which cause problems in processing.

Naturally occurring clays which can be composited with the zeolite L include the montmorillonite and kaolin families which include the sub bentonites, and the kaolins commonly known as Dixie, McNamee, Georgia and Florida clays, or others in which the main mineral constituent is halloysite, kaolinite, dickite, nacrite or anauxite. Such clays can be used in the raw state as originally mined or initially subjected to calcination, acid treatment or chemical modification.

In addition to the foregoing materials, the zeolite L catalyst can be composited with a porous matrix material such as silica-alumina, silica-magnesia, silica-zirconia, silica-thoria, silica-beryllia, silica-titania, as well as ternary compositions such as silica-alumina-thoria, silica-alumina-zirconia, silica-alumina-magnesia and silica-magnesia-zirconia. The matrix can be in the form of a cogel. A mixture of these components could also be used.

The relative proportions of finely divided crystalline silicate and inorganic oxide gel matrix vary widely with the crystalline silicate content ranging from about 0.1 to about 90 percent by weight, and more usually in the range of about 10 to about 70 percent by weight of the composite.

The foregoing zeolite L dehydrocyclization catalyst can be provided in the form of pills, pellets, granules, broken fragments or various special shapes.

The acyclic hydrocarbons to undergo dehydrocyclization in accordance with the present invention are most commonly paraffins but can in general be any acyclic hydrocarbon capable of undergoing ring-closure to provide an aromatic hydrocarbon. Suitable acyclic hydrocarbons include those containing 6 or more carbon atoms per molecule such as $C_{6-20}$ paraffins and $C_{6-20}$ olefins. Specific examples of suitable acyclic hydrocarbons include paraffins such as n-hexane, 2-methylpentane, 3-methylpentane, n-heptane, 2-methylhexane, 3-methylhexane, 3-ethylpentane, 2,5-dimethylhexane, n-octane, 2-methylheptane, 3-methylheptane, 4-methylheptane, 3-ethylhexane, n-nonane, 2-methyloctane, 3-methyloctane, n-decane, and the like, and olefins such as 1-hexane, 2-methyl-1-pentene, 1-heptene, 1-octene, 1-nonene, and the like. The aforementioned acyclic hydrocarbons can be charged to the dehydrocyclization zone individually, in admixture with one or more of the other acyclic hydrocarbons, or in admixture with other hydrocarbons such as naphthenes, aromatics and the like. Thus, mixed hydrocarbon fractions containing significant quantities of acyclic hydrocarbons such as are commonly available in a typical refinery are suitable charge stocks for the process of this invention. Specific examples of such mixed hydrocarbon fractions are highly paraffinic straight-run naphthas, paraffinic raffinates from aromatic extraction or adsorption, $C_6$–$C_9$ paraffin-rich streams and the like refinery streams.

An especially preferred charge stock herein is a paraffin-rich naphtha fraction boiling in the range of about 140° F. to about 350° F. Generally, best results are obtained with a charge stock comprising a mixture of $C_{6-10}$ paraffins, especially $C_6$–$C_8$ paraffins.

The hydrocarbon feedstock is contacted with the Group VIII metal-containing zeolite L catalyst in a dehydrocyclization zone maintained at dehydrocyclization conditions. This contacting may be accomplished by using the catalyst in a fixed bed system, a moving bed system, a fluidized system, or in a batch-type operation. It is also contemplated that the contacting step can be performed in the presence of a physical mixture of particles of a conventional dual-function catalyst of the prior art. In a fixed bed system, the hydrocarbons in the $C_6$ to $C_{11}$ range are preheated by any suitable heating means to the desired reaction temperature and then passed into a dehydrocyclization zone containing a fixed bed of the catalyst. It is, of course, understood that the dehydrocyclization zone may be one or more separate reactors with suitable means therebetween to ensure that the desired conversion temperature is maintained at the entrance to each reactor. It is also important to note that the reactants may be contacted with the catalyst bed in either upward, downward, or radial flow fashion. In addition, the reactants may be in a liquid phase, a mixed liquid-vapor phase, or a vapor phase when they contact the catalyst, with best results obtained in the vapor phase. The dehydrocyclization system then preferably comprises a dehydrocyclization zone containing one or more fixed beds or dense phase moving beds of the catalyst. In a multiple bed system, it is, of course, within the scope of the present invention to use the present catalyst in less than all of the beds with a conventional dual-function catalyst being used in the remainder of the beds. The dehydrocyclization zone may be one or more separate reactors with suitable heating means therebetween to compensate for the endothermic nature of the dehydrocyclization reaction that takes place in each catalyst bed.

The dehydrocyclization reaction is preferably carried out in the presence of a diluent. Although hydrogen is the preferred diluent, in some cases other art-recognized diluents may be advantageously utilized, either individually or in admixture with hydrogen, e.g., $C_1$ to $C_5$ paraffins such as methane, ethane, propane, butane and pentane, etc., and mixtures thereof. Hydrogen is preferred because it serves the dual function of not only lowering the partial pressure of the acyclic hydrocarbon, but also of suppressing the formation of hydrogen-deficient, carbonaceous deposits (i.e., coke) on the catalyst. Ordinarily, hydrogen is utilized in amounts sufficient to insure a hydrogen to hydrocarbon mole ratio of about 0 to about 20:1, with best results obtained in the range of about 2:1 to about 6:1. The hydrogen charged to the dehydrocyclization zone will typically be contained in a hydrogen-rich gas stream recycled from the effluent stream from this zone after a suitable gas/liquid separation step.

The hydrocarbon dehydrocyclization conditions used in the present method include a reactor pressure of about 0.1 atm to about 60 atm, a temperature of about 100 to about 700° C., a weight hourly space velocity (WHSV) of from about 0.5 to about 400 and a hydrogen to hydrocarbon mole ratio of from 0 to about 20.

Reforming generally results in the production of hydrogen. Thus, exogeneous hydrogen need not necessarily be added to the reforming system except for pre-reduction of the catalyst and when the feed is first introduced. Generally, once reforming is underway, part of the hydrogen produced is recirculated over the catalyst. The presence of hydrogen serves to reduce the formation of coke which tends to deactivate the catalyst Hydrogen is preferably introduced into the dehydrocyclization zone at a rate varying from 0 to about 20 moles of hydrogen per mole of hydrocarbon feed. The hydrogen can be in admixture with light gaseous hydrocarbons.

The following examples are illustrative of the dehydrocyclization process herein.

EXAMPLE 1

This example illustrates the preparation of zeolite L in accordance with the procedure of U.S. patent application Ser. No. 124,657 which employs a silica precursor prepared in accordance with the procedure of commonly assigned, copending U.S. patent application Ser. No. 014,147, filed Feb. 12, 1987.

A. Preparation of the Silica Precursor

The silica precipitate precursor for zeolite synthesis was produced using the formulations given in Table 1 as follows:

TABLE 1

| Precursor Synthesis | |
|---|---|
| Solutions | Volume Basis |
| Silicate Solution | |
| Sodium Silicate | |
| (Q-Brand 29 wt % $SiO_2$, 9 wt % $Na_2O$) | 100 |
| 50 wt % NaOH | 1.03 |
| $H_2O$ (Demineralized) | 98.9 |
| Acid Solution | |
| 24 wt % $H_2SO_4$ | 67.0 |

The precursor is prepared in a continuous manner by neutralizing a sodium silicate solution under carefully controlled conditions. The resulting product is a suspension of agglomerated solids in the shape of microspheres. Because of the size and shape, and because primary agglomeration has already taken place, suspensions of these particles exhibit low viscosities at high solids loadings (30 wt %). This is in marked contrast to an equivalent, non-controlled neutralization which results in solid, non-stirrable mass. The particle size of the precursor ranges between 1–500 microns but the average size is 70 microns.

The two solutions were reacted continuously at 30 min. residence time in a plastic vessel equipped with an overflow and mixer. The vessel was filled with water. The silicate solution and the acid solution are pumped into the vessel in a continuous manner. The pH was controlled to about 8. The average residence time of the product is 30 minutes, and it is discharged continuously from the vessel by an overflow tube. The product was collected, filtered and washed with demineralized water to be sulfate free. Analysis of the washed silica precursor is set forth below in Table 2.

TABLE 2

| Analysis of Washed Precursor | |
|---|---|
|  | Wt. Percent |
| Sulfur | 0.005% |
| Silica | 91.3% |
| Alumina | 0.1% |
| Sodium | 1.5% |
| Ash at 1000° F. (542° C.) | 95.53% |

B. Preparation of Zeolite L

The formulation and the conditions used in the synthesis of zeolite L using the foregoing silica precursor are described below.

| Formulation: | |
|---|---|
| Silica Precursor | 1177 gms |
| $Al_2(SO_4)_3 \cdot X H_2O$ | 528 gms |
| 50% NaOH | 428 gms |
| 100% KOH | 643 gms |
| Water | 4676 gms |
| TPA Br | 474 gms |
| Conditions: | |
| Temp., °F. | 220 |
| Solids Content, wt. % | 16 |
| $SiO_2/Al_2O_3$, molar ratio | 22 |
| Crystallization time, hrs | 65 |
| Ultimate Crystal Size, microns | 0.02–0.05 |

Analysis of the product by X-ray diffraction at the end of 65 hours showed it to be identical to zeolite L as reported in the literature. However, the impurities observed in zeolite L prepared in accordance with U.S. Pat. No. 3,216,789, namely zeolite T (offretite type), were noticeably absent.

C. Catalyst Activation and Platinum Addition

The following post-synthesis operations were carried out on the zeolite obtained in accordance with the foregoing procedure (Catalyst B) as well as a quantity of zeolite L which had been synthesized in accordance with U.S. Pat. No. 3,216,789 (Catalyst A).

Both zeolites were precalcined in nitrogen at a heating rate of 5° F./min to 1000° F. and held at this temperature for 3 hours. The calcined materials were then barium exchanged with barium nitrate for 3 hours at 80° C. and a pH of 10. Following the barium exchange, the zeolites were air calcined at a heating rate of 5° F./min to 1000° F. and held at this temperature for 8 hours. Both the excess barium exchange and air calcination operations were repeated for both zeolites. Thereafter, platinum was added to the catalysts by impregnation of the powders by incipient wetness with platinum tetraamine chloride. Following drying at 150° F., both catalysts were calcined at a heating rate of 2° F./min to 500° F. for 2 hours to provide the final catalysts as set forth in Table 3 as follows:

TABLE 3

| Analysis of Zeolite L Catalysts | | |
|---|---|---|
| | Zeolite Prepared by the method of U.S. Pat. No. 3,216,789 (Catalyst A) | Zeolite L Prepared by the method of U.S. Pat. application Ser. No. 124,657 (Catalyst B) |
| $SiO_2/Al_2O_3$, molar | 5.4 | 6 |
| Na, ppm | 100 | 205 |
| K, wt. % | 6.2 | 7.7 |
| Ba, wt. % | 10.8 | 6.1 |
| Pt, wt. % | 1 | 1 |

EXAMPLE 2

Catalysts A and B from Example 1 were employed in the dehydrocyclization of n-hexane (0.02 ppm sulfur). Both catalysts were run with a small bed of $Mn/Al_2O_3$ extrudate upstream to scavenge residual sulfur from the unit. The catalysts were heated to 950° F. in flowing hydrogen. Once the desired temperature and flows were achieved, the n-hexane feedstock was introduced. Products were analyzed on-line by gas chromatography with the results set forth below in Table 4:

TABLE 4

| Product Distribution | | |
|---|---|---|
| | Catalyst A | Catalyst B |
| Dehydrocyclization Conditions | | |
| Temperature, °F. | 950 | 950 |
| Hours on Stream | 35 | 34 |
| WHSV | 3 | 3 |
| Hydrogen:Hydrocarbon ratio | 3 | 3 |
| Pressure, psig | 100 | 100 |
| Product Distribution, Wt. % | | |
| $C_1$ | 3.4 | 2.5 |
| $C_2$ | 2.6 | 2.2 |
| $C_3$ | 3.7 | 2.8 |
| $C_4$ | 3.3 | 2.5 |
| Total, $C_1$–$C_4$ | 13.0 | 10.0 |
| Total Aromatics | 58.9 | 64.6 |
| Selectivity, % | 81.9 | 86.6 |

The foregoing comparison of the product distribution between the conventionally prepared zeolite L (Catalyst A) and the zeolite L prepared in accordance with the procedure of U.S. patent application Ser. No. 124,657 shows that the latter zeolite L catalyst produces less light gases while producing more aromatics. For example, at identical conditions, Catalyst B yields 10 wt. % $C_1$–$C_4$ and 64.6 wt. % total aromatics compared to 13 wt. % and 58.9 wt. %, respectively, for Catalyst A.

The selectivity results listed in Table 4 are defined as the weight percent aromatics in the product divided by the sum of the aromatics plus $C_1$ through $C_4$ produced. Based on the product distribution, Catalyst B produces an aromatic selectivity of over 86% compared to the conventionally prepared Catalyst A which has an aromatic selectivity below 82%.

What is claimed is:

1. A process for the dehydrocyclization of a feed containing one or more acyclic hydrocarbons capable of undergoing ring closure to provide aromatic hydrocarbons which comprises containing the feed under dehydrocyclization conditions with a zeolite L dehydrocyclization catalyst which is substantially free of zeolite T and which contains at least one Group VIII metal component, thereby converting at least a portion of the acyclic hydrocarbon content of the feed to aromatic compound(s), the zeolite L being prepared by the process which comprises:

(a) providing a reaction mixture, said reaction mixture having a solids loading of at least about 15%, wherein solids loading is defined by the formula $$100\% \times \frac{\text{Weight of Silica and Alumina}}{\text{Weight of Total Reaction Mixture}}$$

wherein the reaction mixture comprises a source of silicon, a source of aluminum, and a source of potassium cations, wherein the reaction medium has a composition, expressed in terms of molar ratios of oxides, of

| $SiO_2/Al_2O_3$ | 6 to 30 |
|---|---|
| $OH^-/SiO_2$ | 0.3 to 0.8 |
| $K^+/(K^+ + Na^+)$ | 0.3 to 1 |
| $H_2O/OH^-$ | 10 to 50 |
| $RN/Al_2O_3$ | 0.2 to 2.0 | wherein RN is a source of tetraalkylammonium ion;

(b) maintaining the reaction mixture at about 200° to about 320° F., to produce crystals of zeolite L substantially free of zeolite T; and,
(c) recovering said crystals, said source of silicon being a silica precipitate formed by the process which comprises:
  (1) providing a solution of a silicate;
  (2) providing a precipitate reagent which is effective to precipitate said silicate from said solution;
  (3) maintaining the molar ratio of said silicate to precipitating reagent at least substantially constant; and,
  (4) contacting said silicate solution with a precipitating reagent continuously to effect formation of insoluble silica precipitate, whereby the particle size of said silica precipitate ranges from about 1 to about 500 microns.

2. The process of claim 1 wherein the zeolite L possesses a crystal size having a maximum dimension of less than about 1 micron.

3. The process of claim 1 wherein the Group VIII metal is platinum.

4. The process of claim 1 wherein the zeolite L also contains an alkaline earth metal.

5. The process of claim 1 wherein the zeolite L contains a source of barium.

6. The process of claim 1 wherein the zeolite L is bound with a matrix material.

7. The process of claim 6 wherein the matrix material is selected from the group consisting of alumina-containing and silicon-containing material.

8. The process of claim 1 wherein the dehydrocyclization conditions include a pressure of from about 0.1 to about 60 atm, a temperature of about 100° to about 700° C., a weight hourly space velocity of from about 0.5 to about 400 and a hydrogen to hydrocarbon mole ratio of from 0 to about 20.

9. The process of claim 1 wherein the acyclic hydrocarbon(s) contain from about 6 to about 9 carbon atoms.

10. The process of claim 1 wherein the acyclic hydrocarbon(s) are provided as a naphtha fraction holding in the range of from about 140° F. to about 350° F.

* * * * *